United States Patent
Nishimura et al.

(10) Patent No.: US 9,693,562 B2
(45) Date of Patent: Jul. 4, 2017

(54) LIQUID INSECTICIDE COMPOSITION

(75) Inventors: Kaoru Nishimura, Takoka (JP); Rieko Nakamura, Makinohara (JP); Rie Sakamoto, Hiratsuka (JP)

(73) Assignee: Nippon Soda Co., Ltd., Tokyo (JP)

( * ) Notice: Subject to any disclaimer, the term of this patent is extended or adjusted under 35 U.S.C. 154(b) by 147 days.

(21) Appl. No.: 14/115,590

(22) PCT Filed: May 8, 2012

(86) PCT No.: PCT/JP2012/061758
§ 371 (c)(1),
(2), (4) Date: Nov. 8, 2013

(87) PCT Pub. No.: WO2012/153735
PCT Pub. Date: Nov. 15, 2012

(65) Prior Publication Data
US 2014/0066405 A1  Mar. 6, 2014

(30) Foreign Application Priority Data

May 10, 2011  (JP) .................... 2011-105705

(51) Int. Cl.
*A01N 55/00*    (2006.01)
*A01N 25/30*    (2006.01)
*A01N 47/40*    (2006.01)

(52) U.S. Cl.
CPC ............. *A01N 55/00* (2013.01); *A01N 25/30* (2013.01); *A01N 47/40* (2013.01); *A01N 2300/00* (2013.01)

(58) Field of Classification Search
None
See application file for complete search history.

(56) References Cited

U.S. PATENT DOCUMENTS

| | | | |
|---|---|---|---|
| 7,025,978 | B1 | 4/2006 | Sirinyan et al. |
| 2006/0111323 | A1* | 5/2006 | Sirinyan et al. ............... 514/63 |
| 2006/0257440 | A1 | 11/2006 | Asai et al. |
| 2007/0087937 | A1 | 4/2007 | Leatherman et al. |
| 2007/0135308 | A1 | 6/2007 | Leatherman et al. |
| 2007/0213226 | A1 | 9/2007 | Sieverding et al. |
| 2007/0269467 | A1 | 11/2007 | Leatherman et al. |
| 2008/0242743 | A1 | 10/2008 | Wagner et al. |
| 2009/0069386 | A1 | 3/2009 | Dairiki et al. |
| 2009/0171108 | A1 | 7/2009 | Leatherman et al. |
| 2010/0105555 | A1 | 4/2010 | Giessler-Blank et al. |
| 2010/0204283 | A1* | 8/2010 | Dairiki ................... A01N 25/30 514/357 |
| 2012/0053221 | A1* | 3/2012 | Ishaque et al. ............. 514/407 |
| 2012/0156262 | A1* | 6/2012 | Gutsche ................. A01N 43/56 424/400 |

FOREIGN PATENT DOCUMENTS

| | | |
|---|---|---|
| CN | 101243798 A | 8/2008 |
| CN | 101455207 A | 6/2009 |
| CN | 101554171 A | 10/2009 |
| CN | 101589710 A | 12/2009 |
| CN | 101913942 A | 12/2010 |
| CN | 102113506 A | 7/2011 |
| JP | 04-041406 | 2/1992 |
| JP | 08-092091 | 4/1996 |
| JP | 2003-513990 | 4/2003 |
| JP | 2006131751 A | 5/2006 |
| JP | 2009-500333 | 1/2009 |
| JP | 2009-545517 | 12/2009 |
| JP | 2012180313 A | 9/2012 |
| WO | 2004/100662 | 11/2004 |
| WO | 2007/005470 | 1/2007 |
| WO | 2007/136597 | 11/2007 |
| WO | 2007129395 A1 | 11/2007 |
| WO | 2008111928 A1 | 9/2008 |
| WO | 2009/028454 | 3/2009 |
| WO | 2009085297 A2 | 7/2009 |
| WO | 2010043447 A2 | 4/2010 |
| WO | WO 2010130680 A2 * | 11/2010 |

OTHER PUBLICATIONS

PubChem, 1-Methyl-2-Pyrrolidone, C5H9O, Solubility, excerpt—p. 10; [Downloaded from internet <URL: http://pubchem.ncbi.nlm.nih.gov/compound/13387 >], [Retrieved Feb. 11, 2016], 1 page.*
Wu et al., "Evaluation of Insecticides and Application Methods Against Contarinia Nasturtii (Diptera: Cecidomyiidae ), A New Invasive Insect Pest in the United States", Journal of Economic Entomology, Entomological Society of America, Landham, MD, US, vol. 99, No. 1, Feb. 1, 2006, (Feb. 1, 2006), XP002496283, pp. 117-122.
Srinivasan et al., "Laboratory and Field Evaluations of Silwet L-77 and Kinetic Alone and in Combination With Imidacloprid and Abamectin for the Management of the Asian Citrus Psyllid, Diaphorina Citri (Hemiptera: Psyllidae)", Florida Entomologist, vol. 91, No. 1, Mar. 1, 2008 (Mar. 1, 2008), XP007919307, pp. 87-100.
Vukovic et al., "Insecticidal Effects of a Mixture of Insecticide, Fungicide, Complex Fertilizer, and Wetting Agent Depending on Water Hardness", Database CA [Online] Chemical Abstracts Service, Columbus, Ohio, US, downloaded on Sep. 23, 2014, XP002731205, 2 pages.
Cocco et al., "Toxicity of Organosilicone Adjuvants and Selected Pesticides to the Asian Citrus Psyllid (Hemiptera: Psyllidae) and Its Parasitoid Tamarixia Radiata (Hymenoptera: Eulophidae)", Florida Entomologist, vol. 91, No. 4, Dec. 1, 2008, (Dec. 1, 2008), XP007919316, pp. 610-620.
Wise et al., "Apple: *Malus domestica* Borkhausen, 'Delicious', Control of Codling Moth and Oriental Fruit Moth, 2007", Arthropod Management Tests (AMT), ESA: Entomological Society of America, US, vol. 33, XP009180601, Jan. 1, 2008 (Jan. 1, 2008), pp. A23/1-4.

(Continued)

*Primary Examiner* — Ernst V Arnold
*Assistant Examiner* — Miriam A Levin
(74) *Attorney, Agent, or Firm* — Foley & Lardner LLP

(57) ABSTRACT

A liquid insecticide composition is provided containing a neonicotinoid-based compound, a silicone-based surfactant, and a water-soluble organic solvent. Furthermore, a method is provided for enhancing an insecticidal effect which includes using a silicone-based surfactant in combination with a neonicotinoid-based compound as an insecticidal active ingredient.

12 Claims, No Drawings

(56) References Cited

OTHER PUBLICATIONS

Stanton A. Gill et al., "Verbena, (Annual): Verbena x hybrida, Evaluation of Aria, Talus and Marathon II for Control of Silverleaf Whitefly on Verbena, 2004", Arthropod Management Tests (AMT), ESA: Entomological Society of America, US, vol. 30, Jan. 1, 2005 (Jan. 1, 2005), XP009180594, pp. G45/1-2.

Smitley et al., "YEW: *Taxus x media* L. 'Densiformis', Fletcher Scale on *Taxus*, 2004", Arthropod Management Tests (AMT), ESA: Entomological Society of America, US, vol. 30, Jan. 1, 2005 (Jan. 1, 2005), XP009180595, pp. G46/1-2.

Liu et al., "Insecticidal Activity of Surfactants and Oils Against Silverleaf Whitefly (*Bemisia argentifolii*) Nymphs (Homoptera: Aleyrodidae) on Collards and Tomato", Pest Management Science, 2000, Society of Chemical Industry, vol. 56, No. 10, XP007919318, Oct. 10, 2000 (Oct. 10, 2000), pp. 861-866.

EP Communication with Supplementary European Search Report issued in EP Application No. 12781697.3, dated Oct. 30, 2014, 13 pages.

Office Action issued in JP Application No. 2013-514016, dated Sep. 24, 2014, 6 pages (with EN translation).

Office Action issued in CN Application No. 201280021535.6, dated Aug. 22, 2014, 18 pages (with EN translation).

International Search Report dated Jul. 31, 2012, issued in corresponding PCT Application No. PCT/JP2012/061758.

Decision of Rejection, Office Action in Japanese Application No. 2013-514016, mailed May 19, 2015.

\* cited by examiner

LIQUID INSECTICIDE COMPOSITION

This application is a national stage application of International Application No. PCT/JP2012/061758, filed on May 8, 2012, which claims priority to Japanese Patent Application No. 2011-105705, filed on May 10, 2011, the contents of which are incorporated herein by reference.

TECHNICAL FIELD

The present invention relates to a liquid insecticide composition. More specifically, the invention relates to a liquid insecticide composition which contains a neonicotinoid-based compound such as acetamiprid as an active ingredient, exhibits excellent fast-acting insecticidal activity, and is suitable as a water-soluble liquid formulation.

BACKGROUND ART

Among agrochemical formulations, an emulsifiable concentrate, a wattable powder, a suspension concentrate and the like are known as a formulation which is sprayed after being diluted with water. Among them, a water-soluble liquid formulation (SL liquid formulation) is preferably used from the viewpoint of easy handling and the like. Furthermore, neonicotinoid-based (another name is chloronicotinyl) compounds such as imidacloprid and acetamiprid are known to have excellent insecticidal activity. For this reason, various water-soluble liquid formulations containing the neonicotinoid-based compound as an agrochemical active ingredient have been proposed.

For example, a concentrated water-soluble solution containing imidacloprid, a natural emulsifier based on alkylaryl polyglycol ether, sodium diisooctyl sulfosuccinate, dimethyl sulfoxide and isopropanol (PTL 1, Example 3); a concentrated water-soluble solution containing imidacloprid, sodium diisooctyl sulfosuccinate, dimethyl sulfoxide, triethanolamine salts of alkylbenzene sulfonic acid, sodium salt of alkylbenzene sulfonic acid, condensation product of oleic acid and diethanol amine, and polyethylene glycol (PTL 1, Example 4); an insecticide composition formed of a homogeneous solution which is formed by dissolving acetamiprid in a mixed solvent containing γ-butyrolactone and dimethyl sulfoxide, and by dissolving polyoxyethylene-hardened castor oil or a ethylene oxide propylene oxide block copolymer as a surfactant (PTL 2); an agrochemical composition formed of acetamiprid, polyoxyalkylene alkyl ether, γ-butyrolactone and dipropylene glycol (PTL 3); and a liquid composition for treating a plant-propagating material formed of thiamethoxam, polydimethylsilane, copolymer butanol PO/EO and sodium naphthalenesulfonate (PTL 5) have been proposed.

PRIOR ART LITERATURE

Patent Literature

[PTL 1] Japanese Unexamined Patent Application, First Publication No. H8-92091

[PTL 2] PCT International Publication No. WO2004/100662

[PTL 3] PCT International Publication No. WO2009/028454

[PTL 4] Published Japanese Translation No. 2009-545517 of the PCT International Publication

[PTL 5] Published Japanese Translation No. 2009-500333 of the PCT International Publication

DISCLOSURE OF INVENTION

Problems to be Solved by the Invention

Generally, a neonicotinoid-based compound is known to have a high fast-acting property. However, a liquid composition proposed in the above-described Patent Literature, which contains the neonicotinoid-based compound as an active ingredient, has a poor fast-acting property in some cases. Even if an insecticide is one which can exterminate harmful insects, if the insecticide has a poor fast-acting property, crops suffer feeding damage before the extermination of harmful insects is completed.

Therefore, an object of the invention is to provide a liquid insecticide composition which contains the neonicotinoid-based compounds such as acetamiprid, imidacloprid and thiamethoxam as an active ingredient, exhibits excellent fast-acting insecticidal activity, and is suitable as a water-soluble liquid formulation.

Means for Solving the Problem

Generally, it is considered that when an agricultural and horticultural insecticide is sprayed as a drug solution, a case where an active ingredient comes into direct contact with an insect body is rare, and most of the active ingredient is either adhered onto the plant's surface, soil in which the plants grow or a water surface, or absorbed into the plants. The active ingredient is taken into an insect body and an insecticidal effect is exerted when a harmful insect eats or absorbs liquid. As such, the insecticidal effect of the active ingredient is indirect, thus, it is known that a fast-acting property generally becomes lower.

However, PTL 4 describes that when a silicone-based surfactant of high concentration, specifically 0.1% by mass or higher, is directly applied to harmful insects such as cockroaches and the like, an insecticidal effect is exhibited. In addition, it is proposed that the silicone-based surfactant be used as an additive at the time of formulating a herbicide, a wetting and spreading agent at the time of using a herbicide or an enhancing agent for increasing an effect of a herbicide. However, it has not been found that an insecticidal effect can be obtained when the silicone-based surfactant is used by a method in which the surfactant indirectly acts on insect bodies as described above.

The inventors have carried out thorough studies in order to achieve the above object. As a result, the inventors have found that when using a liquid composition containing a neonicotinoid-based compound, a silicone-based surfactant, and a water-soluble organic solvent as an agricultural and horticultural water-soluble liquid formulation, even if an active ingredient does not come into direct contact with an insect body, an insect can be killed with an excellent knockdown effect and a high fast-acting property. The present invention has been completed by further consideration on the basis of this finding.

That is, the present invention includes the following aspects.

[1] A liquid insecticide composition containing a neonicotinoid-based compound, a silicone-based surfactant, and a water-soluble organic solvent.

[2] The liquid insecticide composition described in [1] in which the neonicotinoid-based compound is acetamiprid.

[3] The liquid insecticide composition described in [1] or [2] in which the silicone-based surfactant is polyether-modified polysiloxane.

[4] The liquid insecticide composition described in [1] or [2] in which the silicone-based surfactant is polyoxyethylene-modified heptamethyltrisiloxane.

[5] The liquid insecticide composition described in [4] in which the silicone-based surfactant is a compound represented by Formula (I).

[Chemical formula 1]

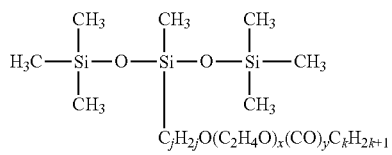

(In Formula (I), j is an integer from 2 to 6, x is an integer from 3 to 10, y is 0 or 1, and k is an integer from 1 to 9.)

[6] The liquid insecticide composition described in any one of [1] to [5] in which the neonicotinoid-based compound is 0.1 parts by mass to 60 parts by mass; the water-soluble organic solvent is 35 parts by mass to 95 parts by mass; and the silicone-based surfactant is 1 part by mass to 15 parts by mass in the total 100 parts by mass of the neonicotinoid-based compound, the water-soluble organic solvent, and the silicone-based surfactant.

[7] The liquid insecticide composition described in any one of [1] to [6] further containing a non-silicone-based nonionic surfactant.

[8] The liquid insecticide composition described in [7] in which a non-silicone-based nonionic surfactant is a polyoxyalkylene block polymer.

[9] The liquid insecticide composition described in [7] or [8] in which the neonicotinoid-based compound is 0.1 parts by mass to 60 parts by mass; the water-soluble organic solvent is 35 parts by mass to 95 parts by mass; and the total amount of the silicone-based surfactant and the non-silicone-based nonionic surfactant is 1 part by mass to 30 parts by mass in the total 100 parts by mass of the neonicotinoid-based compound, the water-soluble organic solvent, the silicone-based surfactant, and the non-silicone-based nonionic surfactant.

[10] The liquid insecticide composition described in any one of [1] to [9] which is used for an agricultural and horticultural application.

[11] A method for enhancing an insecticidal effect including: using a silicone-based surfactant in combination with a neonicotinoid-based compound as an insecticidal active ingredient.

[12] The method for enhancing an insecticidal effect described in [11] in which the silicone-based surfactant is polyoxyethylene-modified heptamethyltrisiloxane.

[13] The method for enhancing an insecticidal effect described in [12] in which the silicone-based surfactant is a compound represented by Formula (I).

[Chemical formula 2]

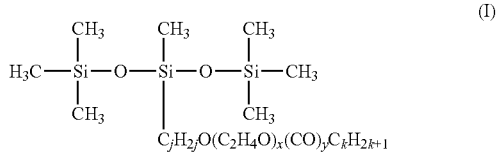

(In Formula (I), j is an integer from 2 to 6, x is an integer from 3 to 10, y is 0 or 1, and k is an integer from 1 to 9.)

Effects of the Invention

The liquid insecticide composition of the invention, even if an active ingredient does not come into direct contact with an insect body, can kill insects with an excellent knockdown effect and a high fast-acting property. The liquid insecticide composition of the invention is preferable as an agricultural and horticultural water-soluble liquid formulation.

BEST MODE FOR CARRYING OUT THE INVENTION

The liquid insecticide composition of the invention contains a neonicotinoid-based compound, a silicone-based surfactant, and a water-soluble organic solvent.

[Neonicotinoid-Based Compound]

The neonicotinoid-based compound used in the invention is a well-known material as an agrochemical active ingredient. Specific examples are acetamiprid, imidacloprid, clothianidin, dinotefuran, thiacloprid, thiamethoxam, nitenpyram and the like. Among them, acetamiprid is preferable.

[Water-Soluble Organic Solvent]

The water-soluble organic solvent used in the invention is not particularly limited as long as the organic solvent is soluble in water and can dissolve the neonicotinoid-based compound. The water-soluble organic solvent having mutual miscibility with water is particularly preferable.

Specific examples of the water-soluble organic solvent include alcohols such as ethanol, n-propanol and isopropanol; glycols such as ethylene glycol, propylene glycol, glycerol; dimethyl sulfoxide; ketones such as acetone, methyl ethyl ketone, cyclohexanone and isophorone; lactones such as γ-butyrolactone; glycol ethers such as diethylene glycol and dipropylene glycol; propylene carbonate; amides such as dimethyl acetamide and dimethyl formamide; and pyrrolidones such as N-methylpyrrolidone. Among them, dimethyl sulfoxide, γ-butyrolactone, dipropylene glycol, dimethylacetamide, and N-methylpyrrolidone are preferable from the viewpoint of low volatility and high safety.

Moreover, if necessary, the liquid insecticide composition of the invention may include organic solvents or water other than the water-soluble organic solvents within a range such that adverse effects such as decreases of solubility of the neonicotinoid-based compound or separation at the time of dilution with water are not exhibited. Furthermore, a water-soluble organic solvent of at least one selected from dimethyl sulfoxide, γ-butyrolactone, dipropylene glycol, dimethylacetamide and N-methylpyrrolidone, and other water-soluble organic solvents such as ethanol or water can be used in combination as a water-soluble organic solvent used in the liquid insecticide composition of the invention.

[Silicone-Based Surfactant]

The silicone-based surfactant used in the invention is preferably a silicone-based nonionic surfactant, more preferably a silicone-based surfactant having a polyorganosiloxane part and polyoxyalkylene part.

Polymethylsiloxane and/or polydimethylsiloxane is preferable as the polyorganosiloxane part. Furthermore, polyethylene oxide and/or polypropylene oxide is preferable as the polyoxyalkylene part.

Specific examples of the silicone-based surfactant include polyether-modified polysiloxane obtained by adding polyoxyalkylene to alkyl hydrogen siloxane; and amino polyether-modified polysiloxane, epoxy polyether-modified polysiloxane and/or carboxy polyether-modified polysiloxane obtained by adding an amino group, an epoxy group and/or a carboxyl group thereto. In addition, a silicone-based surfactant obtained by etherifying or esterifying a terminal hydroxyl group with an alkyl group is exemplified. Examples of a commercially available silicone-based surfactant include Sylgard series (manufactured by Dow Corning Toray Co., Ltd.), Silwet series (Momentive Performance Materials Inc.), Silicone oil KF series (Shin-Etsu Chemical Co., Ltd.), Kinetic (Helena Chemical Company), Siltech (Siltech Co., Ltd.) and the like. An additive at the time of formulating a herbicide, a wetting and spreading agent at the time of using a herbicide, or an enhancing agent for increasing the effect of a herbicide in the related art are included thereto. One kind of these silicone-based surfactants can be used alone, or two or more kinds thereof can be used in combination.

Among them, polyether-modified polysiloxane is preferable, polyoxyethylene-modified heptamethyltrisiloxane is more preferable, and a compound represented by Formula (I) is further preferable.

[Chemical formula 3]

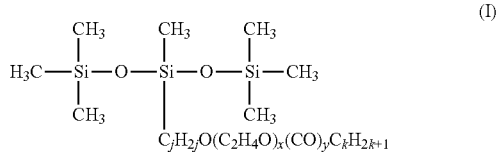

(In Formula (I), j is an integer from 2 to 6, x is an integer from 3 to 10, y is 0 or 1, and k is an integer from 1 to 9.)

It is preferable that the liquid insecticide composition of the invention further contain a non-silicone-based nonionic surfactant.

The non-silicone-based nonionic surfactant is not particularly limited. Examples of the non-silicone-based nonionic surfactant include polyoxyethylene alkyl ether, polyoxyalkylene alkyl ether, polyoxyethylene alkyl aryl ether, polyoxyethylene styryl phenyl ether, polyoxyethylene vegetable oil ether, polyoxyethylene fatty acid ester, polyoxyethylene sorbitan fatty acid ester, polyoxyethylene phenyl ether polymer, polyoxyethylene alkylene aryl phenyl ether, polyoxyalkylene aryl phenyl ether, polyoxyethylene alkylene glycol, polyoxyethylene polyoxypropylene block polymer, acetylene glycol-based surfactant (2,4,7,9-tetramethyl-decyne-4,7-diol and the like) and the like.

Among them, polyoxyalkylene block polymer is preferable. Polyoxyalkylene block polymer is a compound which is formed by block copolymerization of monomers such as ethylene oxide, propylene oxide and butylene oxide, or which is formed by further etherification of one terminal hydroxyl group with an alkyl group or an alkenyl group. There are various kinds of compounds according to the number of a block and a bonding order. Specific examples are Pluronic series (registered trademark, manufactured by BASF) and the like.

One kind of non-silicone-based nonionic surfactant can be used alone, or two or more kinds thereof can be used in combination.

The mass ratio of a silicone-based surfactant/a non-silicone-based nonionic surfactant is preferably 100/0 to 30/70, more preferably 100/0 to 50/50.

Moreover, if necessary, a non-silicone-based surfactant other than the silicone-based surfactant and the non-silicone-based nonionic surfactant can be added to the liquid insecticide composition of the invention.

Examples of other non-silicone-based surfactants include non-silicone-based cationic surfactants such as alkylamine ethylene oxide adducts such as a tallow amine ethylene oxide adduct, an oleyl amine ethylene oxide adduct, a soy amine ethylene oxide adduct, a cocoamine ethylene oxide adduct, a synthetic alkylamine ethylene oxide adduct, an octyl amine ethylene oxide adduct; an alkyl amine propylene oxide adduct; quaternary ammonium compounds derived from these compounds; and mixtures thereof; non-silicone-based anionic surfactants such as a polycarboxylic acid-type surfactant, lignin sulfonate, alkyl aryl sulfonate, dialkyl sulfosuccinate, polyoxyethylene alkyl aryl ether sulfates, alkyl naphthalene sulfonate, polyoxyethylene styryl phenyl ether sulfate, alkyl benzene sulfonate, alkyl sulfate; non-silicone-based amphoteric surfactants such as lauryl dimethyl amine oxide, Armox C/12, amine oxide, Monaterics, Miranols, betaine, Lonzaines and mixtures thereof.

[Other Ingredients]

The liquid insecticide composition of the invention, within a range which does not impair the effects of the invention, can contain adjuvants such as an ultraviolet absorber, an antioxidant, a preservative, an enhancing agent, a colorant, a fragrance, a binder, a thickener and a viscosity modifier.

Furthermore, the liquid insecticide composition of the invention, within a range which does not impair the effects of the invention, can contain an agrochemical active ingredient other than neonicotinoid-based compounds. Examples of other agrochemical active ingredient include a germicide, a fungicide, a bactericidal agent, an acaricide, an insecticide, a herbicide, a growth regulator and the like.

The liquid insecticide composition of the invention is not particularly limited by the composition ratio of a neonicotinoid-based compound, a water-soluble organic solvent and a silicone-based surfactant; however, a preferable composition ratio is as follows. A neonicotinoid-based compound is preferably 0.1 parts to 60 parts by mass, more preferably 9 parts to 20 parts by mass and further preferably 10 parts to 15 parts by mass; a water-soluble organic solvent is preferably 35 parts to 95 parts by mass, more preferably 65 parts to 90 parts by mass and further preferably 70 parts to 85 parts by mass; a silicone-based surfactant is preferably 1 part to 15 parts by mass, and more preferably 2 parts to 10 parts by mass, in the total 100 parts by mass of a neonicotinoid-based compound, a water-soluble organic solvent and a silicone-based surfactant.

Moreover, the liquid insecticide composition of the invention is not particularly limited by the composition ratio of a neonicotinoid-based compound, a water-soluble organic solvent, a silicone-based surfactant and a non-silicone-based surfactant; however, a preferable composition ratio is as follows. A neonicotinoid-based compound is preferably 0.1 parts to 60 parts by mass, more preferably 9 parts to 20 parts by mass and further preferably 10 parts to 15 parts by mass; a water-soluble organic solvent is preferably 35 parts to 95 parts by mass, more preferably 65 parts to 90 parts by mass and further preferably 70 parts to 85 parts by mass; the total amount of a silicone-based surfactant and a non-silicone-based nonionic surfactant is preferably 1 part to 30 parts by mass, more preferably 1 part to 15 parts by mass and further preferably 5 parts to 15 parts by mass, in the total 100 parts by mass of a neonicotinoid-based compound, a water-soluble organic solvent, a silicone-based surfactant and a non-silicone-based nonionic surfactant.

In the composition ratio as described above, it is possible to dissolve a neonicotinoid-based compound at high concentration without inactivating the neonicotinoid-based compound. When the composition is diluted with water, cloudiness or precipitation hardly occurs, and it is possible to reliably exhibit a fast-acting insecticidal effect, which is the primary object of the invention.

The preparation method for a liquid insecticide composition of the invention is not particularly limited as long as the method can homogeneously dissolve respective ingredients, and can be suitably selected from well-known preparation methods. For example, it is possible to prepare a liquid insecticide composition by mixing and stirring the above-described respective ingredients in a container. A mixing order, a stirring method, a container and the like are not particularly limited, and are arbitrary.

[Method for Use]

The liquid insecticide composition of the invention can be used as a water-soluble liquid formulation (SL liquid formulation) as is or by diluting with water.

When the liquid insecticide composition of the invention is applied by a method in which the liquid insecticide composition comes into direct contact with an insect body, a fast-acting insecticidal effect is naturally exerted. Even in a case where an indirect acting method on an insect body in which the liquid insecticide composition of the invention is adhered to a seed, a plant body and soil in which a plant grows or water surface or absorbed into plants by spraying is applied, an excellent fast-acting insecticidal effect is exerted. Accordingly, the liquid insecticide composition of the invention is particularly suitable for agricultural and horticultural application.

Furthermore, the liquid insecticide composition of the invention can be applied with a germicide, an insecticide, a herbicide, a spreading agent, a fertilizer, a soil conditioner and the like.

The liquid insecticide composition of the invention can be used in any of an agricultural land treatment or a non-agricultural land treatment.

In an agricultural land treatment, the liquid insecticide composition of the invention can be used as a seed treatment agent used in a blasting treatment to seed tubers and the like, a powder coating treatment, a spray coating, a dip immersion treatment; as a stem and leaf treatment agent used in a spray treatment, a top dressing treatment and the like; as a soil treatment agent used in a surface spray treatment, a mixing treatment, an irrigation treatment, a fumigation treatment, a hole treatment, a plant foot treatment, a row treatment, a seeding furrow treatment, a raising seedling box, a seedling-raising pot treatment and the like; as a paddy field treatment agent used in a granule treatment, a jumbo agent treatment, a suspension concentrate treatment and the like; as other agents used in a fumigation treatment, a treatment for lawns and the like.

In a non-agricultural land treatment, the liquid insecticide composition of the invention can be used as a soil pesticide, a termite control agent, a pest control agent, a wood pest control agent, a bait agent, an animal ectoparasite-controlling agent, a sanitary pest control agent and the like. If necessary, the liquid insecticide composition of the invention can be used as a household sanitary agent, an algae-controlling agent for fishing nets and the like, an antifungal agent for wood by using in combination with other harmful organism controlling agents.

An applied amount of the liquid insecticide composition of the invention is different according to concentration of a neonicotinoid-based compound, weather conditions at the time of applying, an applying method, an applying site, a control target disease, a target crop and the like; however, the amount of the neonicotinoid-based compound per hectare is usually 1 g to 1000 g and preferably 10 g to 100 g.

A method for enhancing an insecticidal effect of the invention is a method which includes using a silicone-based surfactant in combination with a neonicotinoid-based compound as an insecticidal active ingredient. In the method, the silicone-based surfactant is preferably polyoxyethylene-modified heptamethyltrisiloxane, and more preferably a compound represented by Formula (I).

Examples of methods of using in combination include a method in which just before application to agricultural land, a water-soluble organic solvent solution of the neonicotinoid-based compound and the silicone-based surfactant are mixed in a predetermined ratio in which the neonicotinoid-based compound is preferably 0.1 parts to 60 parts by mass, more preferably 9 parts to 20 parts by mass, and further preferably 10 parts to 15 parts by mass; the water-soluble organic solvent is preferably 35 parts to 95 parts by mass, more preferably 65 parts to 90 parts by mass, and further preferably 70 parts to 85 parts by mass; a silicone-based surfactant is preferably 1 part to 15 parts by mass, and more preferably 2 parts to 10 parts by mass in the total 100 parts by mass of the neonicotinoid-based compound, the water-soluble organic solvent, and the silicone-based surfactant, and next, the resultant is applied to agricultural land and the like; and a method in which a water-soluble organic solvent solution of the neonicotinoid-based compound and solution of the silicone-based surfactant are applied to agricultural land and the like at the same time or before and after. Furthermore, a non-silicone-based surfactant may be included in the water-soluble organic solvent solution of the neonicotinoid-based compound or the solution of the silicone-based surfactant.

EXAMPLES

Next, Examples are shown below, whereby the present invention will be more specifically described. However, the present invention is not limited by these Examples.

Example 1

10 parts by mass of acetamiprid (purity is 99.8%; manufactured by Nippon Soda Co., Ltd.) was added to a mixed solvent formed of 50 parts by mass of γ-butyrolactone and 30 parts by mass of dipropylene glycol, and the resultant was stirred to dissolve. 5 parts by mass of polyoxyethylene polyoxypropylene block polymer as a non-silicone-based nonionic surfactant and 5 parts by mass of polyoxyethylene-modified heptamethyltrisiloxane having a structure represented by Formula (I) as a silicone-based surfactant were added thereto, and the resultant was stirred to dissolve, thereby obtaining a homogeneous liquid insecticide composition.

Comparative Example 1

A homogeneous liquid insecticide composition was obtained in the same manner as in Example 1 except that 5 parts by mass of polyoxyethylene tridecyl ether (HLB 10.5) was used instead of 5 parts by mass of polyoxyethylene-modified heptamethyltrisiloxane.

Comparative Example 2

5 parts by mass of polyoxyethylene polyoxypropylene block polymer as a non-silicone-based nonionic surfactant and 5 parts by mass of polyoxyethylene-modified heptamethyltrisiloxane as a silicone-based surfactant were added to a mixed solvent formed of 56.25 parts by mass of γ-butyrolactone and 33.75 parts by mass of dipropylene glycol, and the resultant was stirred to dissolve. A liquid composition was obtained by diluting this solution to 1000 times with water.

Comparative Example 3

1 part by mass of polyoxyethylene-modified heptamethyltrisiloxane having a structure represented by Formula (I) as a silicone-based surfactant was added to 99 parts by mass of a liquid composition obtained in Comparative Example 2, and the resultant was stirred to dissolve, thereby obtaining a homogeneous liquid insecticide composition.

Test Example 1

Physical Property

The liquid insecticide composition obtained in Example 1 was diluted to 1000 times with water. Surface tension and a contact angle thereof were measured. The liquid insecticide composition obtained in Comparative Example 1 was diluted to 1000 times with water. Surface tension and a contact angle thereof were measured. The results thereof are shown in TABLE 1. Moreover, the contact angle is a value measured one minute after the liquid to be measured was dropped onto a paraffin piece.

TABLE 1

| Drug | Surface tension | Contact angle [°] |
| --- | --- | --- |
| Example 1 | 23.3 | 43 |
| Comparative Example 1 | 27.1 | 46 |
| Purified water | 70.6 | 109 |

Test Example 2

Control Test

The liquid insecticide composition obtained in Example 1 was diluted to 1000 times with water to obtain a diluted acetamiprid solution of a concentration of 100 ppm. The liquid insecticide composition obtained in Comparative Example 1 was diluted to 1000 times with water to obtain a diluted acetamiprid solution of a concentration of 100 ppm.

Respective diluted solutions were sprayed to bok choy (qinggengcai) with a glass nozzle, and were air-dried. Thereafter, five striped flea beetle adults were inoculated, respectively. Testing was performed two times for respective diluted solutions, observation was performed after elapsed times shown in TABLE 2 from the inoculation, and a mortality rate of insects, a knock down rate of insects, and the number of insect feeding traces were obtained. The results thereof are shown in TABLE 2. A mortality rate of insects and a knock down rate of insects are average values of two measurements, and the number of insect feeding traces is a sum of two measurements.

TABLE 2

| | Elapsed time | | | | | | | | | |
| --- | --- | --- | --- | --- | --- | --- | --- | --- | --- | --- |
| | For 30 minutes | | For 3 hours | | For 1 day | | For 2 days | | For 3 days | |
| Drug | Mortality (knock down) rate of insects | Number of insect feeding traces | Mortality (knock down) rate of insects | Number of insect feeding trace | Mortality (knock down) rate of insects | Number of insect feeding trace | Mortality (knock down) rate of insects | Number of insect feeding trace | Mortality (knock down) rate of insects | Number of insect feeding trace |
| Example 1 | 0 (70) | 0 | 0 (70) | 0 | 0 (90) | 6 | 90 (0) | 14 | 100 (0) | 14 |
| Comparative Example 1 | 0 (60) | 0 | 0 (50) | 1 | 0 (70) | 13 | 60 (20) | 27 | 70 (0) | 35 |
| Tap water | 0 (0) | 18 | 0 (0) | 31 | 0 (0) | 187 | 0 (0) | 384 | 0 (0) | 481 |

Test Example 3

Control Comparative Test

Respective liquid compositions obtained in Comparative Example 2 and Comparative Example 3 were sprayed to bok choy (qinggengcai) with a glass nozzle, and were air-dried. Thereafter, five striped flea beetle adults were inoculated to the bok choy (qinggengcai), respectively. Observation was performed after elapsed times shown in TABLE 3 from the inoculation, and a mortality rate of insects, a knock down rate of insects, and the number of insect feeding traces were obtained. The test was performed two times for respective diluted solutions. The results thereof are shown in TABLE 3.

TABLE 3

| | Elapsed time | | | | | |
|---|---|---|---|---|---|---|
| | For 2 hours | | For 1 day | | For 2 days | |
| Drug | Mortality (knock down) rate of insects | Number of insect feeding trace | Mortality (knock down) rate of insects | Number of insect feeding trace | Mortality (knock down) rate of insects | Number of insect feeding trace |
| Comparative Example 2 | 0 (0) | 8 | 0 (0) | 78 | 0 (0) | 241 |
| Comparative Example 3 | 0 (0) | 9 | 0 (0) | 89 | 0 (0) | 239 |
| Tap water | 0 (0) | 10 | 0 (0) | 115 | 0 (0) | 299 |

Test Example 4

Control Reference Test

Five striped flea beetle adults were immersed in respective liquid compositions obtained in Comparative Example 2 and Comparative Example 3 for about 20 seconds. Thereafter, the five striped flea beetle adults were inoculated to bok choy (qinggengcai), respectively. Observation was performed after elapsed times shown in TABLE 4 from the inoculation, and a mortality rate of insects, a knock down rate of insects, and the number of insect feeding traces were obtained. The test was performed two times for respective diluted solutions. The results thereof are shown in TABLE 4.

TABLE 4

| | Elapsed time | | | | | |
|---|---|---|---|---|---|---|
| | For 2 hours | | For 1 day | | For 2 days | |
| Drug | Mortality (knock down) rate of insects | Number of insect feeding trace | Mortality (knock down) rate of insects | Number of insect feeding trace | Mortality (knock down) rate of insects | Number of insect feeding trace |
| Comparative Example 2 | 0 (0) | 12 | 0 (0) | 110 | 0 (0) | 308 |
| Comparative Example 3 | 0 (0) | 14 | 0 (0) | 97 | 0 (0) | 321 |

It took a longer time for a knock down and mortality rate of insects to reach 80% in the liquid insecticide composition obtained in Comparative Example 1 compared to the liquid insecticide composition obtained in Example 1. In addition, the liquid insecticide composition obtained in Comparative Example 1 tends to have the higher number of feeding damage traces also. Therefore, it was found that the liquid insecticide composition obtained in Example 1 exhibits a knockdown effect with a high fast-acting property compared to the liquid insecticide composition obtained in Comparative Example 1.

On the other hand, even in a case where the liquid composition obtained in Comparative Example 2 using only a silicone-based surfactant and the liquid composition obtained in Comparative Example 3 containing a silicone-based surfactant of high concentration were directly applied to an insect body, an insecticidal effect was not seen at all.

INDUSTRIAL APPLICABILITY

The liquid insecticide composition of the invention, even if an active ingredient does not come into direct contact with an insect body, can kill insects with an excellent knockdown effect and a high fast-acting property. The liquid insecticide composition of the invention is preferable as an agricultural and horticultural water-soluble liquid formulation. Therefore, the liquid insecticide composition of the invention is industrially useful.

The invention claimed is:

1. A liquid insecticide composition consisting of a neonicotinoid-based compound, a silicone-based surfactant, a water-soluble organic solvent, and a non-silicone-based nonionic surfactant, wherein the water-soluble organic solvent is a lactone or a mixture of a lactone and at least one organic solvent selected from the group consisting of alcohols, glycols, ketones, glycol ethers, propylene carbonate, amides, and pyrrolidones, wherein the silicone-based surfactant is polyoxyethylene-modified heptamethyltrisiloxane, and wherein the neonicotinoid-based compound is 0.1 parts by mass to 60 parts by mass; the water-soluble organic solvent is 35 parts by mass to 95 parts by mass; and the total amount of the silicone-based surfactant and the non-silicone-based nonionic surfactant is 1 part by mass to 30 parts by mass in the total 100 parts by mass of the neonicotinoid-based compound, the water-soluble organic solvent, the silicone-based surfactant, and the non-silicone-based nonionic surfactant.

2. The liquid insecticide composition according to claim 1, wherein the neonicotinoid-based compound is acetamiprid.

3. The liquid insecticide composition according to claim 2, wherein the silicone-based surfactant is a compound represented by Formula (I):

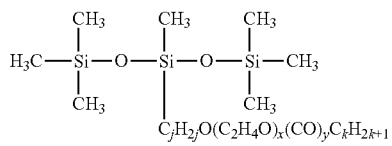

in Formula (I), j is an integer from 2 to 6, x is an integer from 3 to 10, y is 0 or 1, and k is an integer from 1 to 9.

4. The liquid insecticide composition according to claim 2, wherein the non-silicone-based nonionic surfactant is a polyoxyalkylene block polymer.

5. The liquid insecticide composition according to claim 2, wherein the neonicotinoid-based compound is 10 parts by mass to 15 parts by mass; the water-soluble organic solvent is 70 parts by mass to 85 parts by mass; and the total amount of the silicone-based surfactant and the non-silicone-based nonionic surfactant is 5 parts by mass to 15 parts by mass in the total 100 parts by mass of the neonicotinoid-based compound, the water-soluble organic solvent, the silicone-based surfactant, and the non-silicone-based nonionic surfactant.

6. The liquid insecticide composition according to claim 1, wherein the silicone-based surfactant is a compound represented by Formula (I):

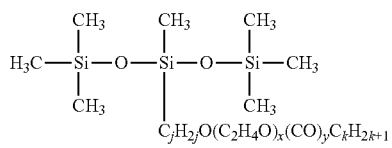

in Formula (I), j is an integer from 2 to 6, x is an integer from 3 to 10, y is 0 or 1, and k is an integer from 1 to 9.

7. The liquid insecticide composition according to claim 1, wherein the non-silicone-based nonionic surfactant is a polyoxyalkylene block polymer.

8. The liquid insecticide composition according to claim 1, wherein the neonicotinoid-based compound is 10 parts by mass to 15 parts by mass; the water-soluble organic solvent is 70 parts by mass to 85 parts by mass; and the total amount of the silicone-based surfactant and the non-silicone-based nonionic surfactant is 5 parts by mass to 15 parts by mass in the total 100 parts by mass of the neonicotinoid-based compound, the water-soluble organic solvent, the silicone-based surfactant, and the non-silicone-based nonionic surfactant.

9. The liquid insecticide composition according to claim 1, which is used for an agricultural and horticultural application.

10. The liquid insecticide composition according to claim 1, wherein the lactone is γ-butyrolactone.

11. A method for enhancing an insecticidal effect comprising: using the liquid insecticide composition of claim 1.

12. The method for enhancing an insecticidal effect according to claim 11, wherein the silicone-based surfactant is a compound represented by Formula (I):

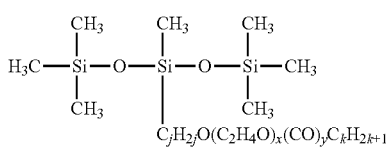

in Formula (I), j is an integer from 2 to 6, x is an integer from 3 to 10, y is 0 or 1, and k is an integer from 1 to 9.

* * * * *